US011139080B2

(12) United States Patent
Carlson et al.

(10) Patent No.: US 11,139,080 B2
(45) Date of Patent: Oct. 5, 2021

(54) SYSTEM FOR DECISION MANAGEMENT

(71) Applicant: OrthoScience, Inc., Mill Valley, CA (US)

(72) Inventors: Sean Carlson, Mill Valley, CA (US); Ross Miller, Sunnyvale, CA (US)

(73) Assignee: OrthoScience, Inc., Mill Valley, CA (US)

( * ) Notice: Subject to any disclaimer, the term of this patent is extended or adjusted under 35 U.S.C. 154(b) by 0 days.

(21) Appl. No.: 15/848,958

(22) Filed: Dec. 20, 2017

(65) Prior Publication Data
US 2019/0189276 A1 Jun. 20, 2019

(51) Int. Cl.
| | |
|---|---|
| G16H 30/40 | (2018.01) |
| G16H 50/20 | (2018.01) |
| G16H 30/20 | (2018.01) |
| G06T 11/00 | (2006.01) |
| G16H 20/40 | (2018.01) |
| G16H 50/70 | (2018.01) |
| G16H 15/00 | (2018.01) |
| G16H 10/60 | (2018.01) |

(52) U.S. Cl.
CPC .......... *G16H 50/20* (2018.01); *G06T 11/003* (2013.01); *G16H 10/60* (2018.01); *G16H 15/00* (2018.01); *G16H 20/40* (2018.01); *G16H 30/20* (2018.01); *G16H 30/40* (2018.01); *G16H 50/70* (2018.01)

(58) Field of Classification Search
CPC .......... A61C 7/002; A61C 7/00; A61C 19/04; A61C 9/004
See application file for complete search history.

(56) References Cited

U.S. PATENT DOCUMENTS

| | | | |
|---|---|---|---|
| 6,682,196 B2 | 1/2004 | Sheets, Jr. et al. | |
| 6,698,889 B2 | 3/2004 | Pettit et al. | |
| 7,343,305 B2 | 3/2008 | Benn et al. | |
| 7,756,727 B1 | 7/2010 | Greenspan et al. | |
| 7,792,687 B2 | 9/2010 | Farris et al. | |
| 7,953,612 B1 | 5/2011 | Palmese et al. | |
| 7,987,099 B2 | 7/2011 | Kuo et al. | |
| 8,021,147 B2 | 9/2011 | Sporbert et al. | |
| 8,075,306 B2* | 12/2011 | Kitching | A61C 7/002 |
| | | | 433/24 |
| 8,099,305 B2 | 1/2012 | Kuo et al. | |
| 8,152,523 B2 | 4/2012 | Sporbert et al. | |
| 8,189,883 B2 | 5/2012 | Oosawa et al. | |
| 8,380,013 B2 | 2/2013 | Hisanaga et al. | |
| 8,392,216 B2 | 3/2013 | Crockett | |
| 8,655,682 B2 | 2/2014 | Srivastava et al. | |
| 8,660,857 B2 | 2/2014 | Ebadollahi et al. | |
| 8,744,867 B2 | 6/2014 | Spertus | |
| 8,793,245 B2 | 7/2014 | Kwete | |
| 8,843,381 B2 | 9/2014 | Kuo et al. | |

(Continued)

*Primary Examiner* — Reginald R Reyes
(74) *Attorney, Agent, or Firm* — Levine Bagade Han LLP

(57) ABSTRACT

A system for decision management is described which enables a practitioner to collaborate on treatment options and outcomes. The practitioner may access a remote server through any number of electronic devices, e.g., smart phone, computer, tablet, personal digital assistant, etc. to conduct any number of searches for related treatments of interest, use of products during treatments, one or more particular doctors, condition of a patient at a starting point, resulting outcome from treatments, or any other number of conditions or features.

28 Claims, 16 Drawing Sheets

(56) References Cited

U.S. PATENT DOCUMENTS

| | | | |
|---|---|---|---|
| 8,863,031 | B2 | 10/2014 | Douen |
| 8,874,452 | B2 | 10/2014 | Kuo |
| 8,934,695 | B2 | 1/2015 | Sato et al. |
| 8,953,857 | B2 | 2/2015 | Kondo et al. |
| 9,008,390 | B2 | 4/2015 | Takata et al. |
| 9,111,027 | B2 | 8/2015 | Kozuka et al. |
| 9,250,172 | B2 | 2/2016 | Harris et al. |
| 9,418,150 | B2 | 8/2016 | Charlot et al. |
| 9,589,104 | B2 | 3/2017 | Heywood et al. |
| 9,594,871 | B2 | 3/2017 | Takata et al. |
| 2003/0149597 | A1 | 8/2003 | Zaleski |
| 2004/0006432 | A1* | 1/2004 | Lau .................. G16H 30/20 702/19 |
| 2004/0044547 | A1 | 3/2004 | Klennert et al. |
| 2004/0259049 | A1* | 12/2004 | Kopelman .............. A61C 7/00 433/24 |
| 2006/0241978 | A1 | 10/2006 | Yoshii |
| 2007/0128574 | A1* | 6/2007 | Kuo ................... G16H 50/70 433/24 |
| 2008/0172386 | A1 | 7/2008 | Ammar et al. |
| 2008/0270175 | A1 | 10/2008 | Rodriguez et al. |
| 2008/0305454 | A1* | 12/2008 | Kitching ................ A61C 7/00 433/24 |
| 2009/0012815 | A1 | 1/2009 | Voegeli |
| 2009/0076846 | A1 | 3/2009 | Bentwich et al. |
| 2009/0106225 | A1 | 4/2009 | Smith et al. |
| 2009/0259488 | A1 | 10/2009 | Gounares et al. |
| 2009/0276246 | A1 | 11/2009 | Haskell et al. |
| 2010/0235183 | A1 | 9/2010 | Firminger et al. |
| 2010/0235184 | A1 | 9/2010 | Firminger et al. |
| 2010/0312798 | A1 | 12/2010 | Dutta et al. |
| 2011/0046979 | A1 | 2/2011 | Tulipano et al. |
| 2011/0099032 | A1 | 4/2011 | Miyasa et al. |
| 2011/0238433 | A1 | 9/2011 | Voegeli |
| 2012/0041772 | A1 | 2/2012 | Ebadollahi et al. |
| 2012/0158433 | A1 | 6/2012 | Schmieding et al. |
| 2012/0221349 | A1 | 8/2012 | Eric |
| 2012/0226113 | A1 | 9/2012 | Pandya |
| 2012/0239435 | A1 | 9/2012 | Ennett et al. |
| 2012/0245958 | A1 | 9/2012 | Lawrence et al. |
| 2012/0316891 | A1 | 12/2012 | Friedlander et al. |
| 2013/0093829 | A1* | 4/2013 | Rosenblatt ............ G06T 7/0012 348/14.01 |
| 2013/0173235 | A1 | 7/2013 | Freezer |
| 2013/0226612 | A1 | 8/2013 | Carmeli et al. |
| 2013/0262141 | A1 | 10/2013 | Crockett |
| 2013/0268547 | A1 | 10/2013 | Boroczky et al. |
| 2014/0039921 | A1 | 2/2014 | Broverman et al. |
| 2014/0234801 | A1 | 8/2014 | Herrington et al. |
| 2014/0244292 | A1 | 8/2014 | Rosenberg et al. |
| 2014/0324469 | A1 | 10/2014 | Reiner |
| 2014/0350954 | A1 | 11/2014 | Ellis et al. |
| 2014/0378737 | A1 | 12/2014 | Carpenter et al. |
| 2014/0379356 | A1 | 12/2014 | Sachdeva et al. |
| 2015/0073816 | A1 | 3/2015 | Ha et al. |
| 2015/0088534 | A1 | 3/2015 | Spertus |
| 2015/0132708 | A1 | 5/2015 | Kuo |
| 2015/0242580 | A1 | 8/2015 | David et al. |
| 2016/0034648 | A1 | 2/2016 | Mohlenbrock et al. |
| 2016/0103973 | A1 | 4/2016 | Singal et al. |
| 2016/0300022 | A1 | 10/2016 | Fung et al. |
| 2016/0314588 | A1 | 10/2016 | Harper |
| 2016/0321427 | A1 | 11/2016 | Bogoni et al. |
| 2016/0378945 | A1 | 12/2016 | Mian et al. |
| 2017/0011187 | A1 | 1/2017 | Oosawa |
| 2017/0068789 | A1 | 3/2017 | Dalton et al. |
| 2017/0076046 | A1 | 3/2017 | Barnes et al. |
| 2017/0100208 | A1* | 4/2017 | Wen ...................... A61C 7/002 |
| 2017/0140536 | A1 | 5/2017 | Takata et al. |
| 2017/0169181 | A1 | 6/2017 | Shumer et al. |
| 2018/0036097 | A1* | 2/2018 | Kim .................... A61C 1/0015 |

\* cited by examiner

SYSTEM FOR DECISION MANAGEMENT

FIELD OF THE INVENTION

The present invention relates to methods and apparatus for supporting clinical decision-making. More particularly, the present invention relates to methods and apparatus for presenting information to and providing interaction with a user to facilitate clinical decision-making by the user across a range of treatments, products, and clinicians through a database that provides evidence and discussion for users to share information on various treatment outcomes.

BACKGROUND OF THE INVENTION

In making clinical decisions for a patient, the practitioner generally selects an appropriate treatment course of action after weighing the benefits and risks of one or more alternate approaches. However, there is usually some uncertainty involved in making such clinical decisions due to any number of known and unknown factors. Additionally, outcomes may vary depending upon the types of treatment applied, patient compliance, length of treatment, etc. Moreover, in the context of orthodontic treatments, outcomes may vary depending upon the type of oral prosthesis or device utilized.

A number of systems exist which attempt to perform data mining, trend extraction, as well as matching one patient with a plurality of other patients having similar pathologies. However, these systems fail to provide a platform which allows for a user to not only search for similar treatment modalities, but also enables the interaction between users.

Accordingly, there exists a need for methods and devices which address the shortcomings of prior systems. There is also a need for methods that allow easy comparison of initial and final states, what treatment was applied, and a comparison of final outcomes.

SUMMARY OF THE INVENTION

In treating a malocclusion or any abnormality in the dentition of a subject, the orthodontic or dental practitioner may typically diagnose the patient and then perform one or more treatments upon the subject's dentition based upon the experience of the practitioner in making any clinical decision. However, given the range of treatments, number of different products used effecting treatment, and variability in patient anatomy and treatment response, the practitioner may benefit from the experience of other practitioners in their clinical decision-making.

An example of a system which enables a practitioner to collaborate on treatment options and outcomes may be provided where the practitioner may access a remote server through any number of electronic devices, e.g., smart phone, computer, tablet, personal digital assistant, etc. to conduct any number of searches for related treatments of interest, use of products during treatments, one or more particular doctors, condition of a patient at a starting point, resulting outcome from treatments, or any other number of conditions or features.

To facilitate the collaboration of treatment options and outcomes, the patient-related information, treatment parameters, treatment outcome, etc. may be formed into a case card. One method of forming a case card may generally comprise receiving from a user one or more parameters relating to a treatment performed upon an oral or maxillofacial region of a subject, the one or more parameters including at least an initial position of the oral or maxillofacial region prior to a treatment, products or appliances used, and at least a final position of the oral or maxillofacial region upon completion of the treatment, forming an animation which illustrates a movement of the oral or maxillofacial region from the initial position to the final position based upon the one or more parameters, associating the animation with the one or more parameters within the case card, and displaying the animation within the case card. The case card may contain all the information the user can upload regarding the individual patient's treatment.

One variation of a system for facilitating collaboration with the case cards may generally comprise a non-transitory computer readable medium for storing computer readable program code, and a processor in communication with the non-transitory computer readable medium, the processor being configured to perform operations including: receiving one or more parameters relating to a treatment performed upon an oral or maxillofacial region of a subject, the one or more parameters including at least an initial position of the oral or maxillofacial region prior to a treatment and at least a final position of the oral or maxillofacial region upon completion of the treatment; associating an animation with the one or more parameters within the case card, wherein the animation illustrates a movement of the oral or maxillofacial region from the initial position to the final position based upon the one or more parameters; and displaying the animation within the case card.

In addition to the case cards, exchange of comments or observations between two or more users may be facilitated by the use of theory cards. The theory cards may function as place holders for comments, observations, ideas, concepts, theories, etc. based on evidence from several idea cards. One method of forming a theory card may generally comprise receiving from a user one or more terms relating to a treatment of interest, displaying one or more case cards associated with at least one of the terms, wherein the one or more case cards each comprise one or more parameters relating to the treatment of interest performed upon a dentition of a subject, the one or more parameters including at least an initial position of the dentition prior to a treatment and at least a final position of the dentition upon completion of the treatment, presenting at least two of the case cards selected for comparison by the user, receiving one or more comments or observations from the user relating to the two or more case cards being compared, and associating the one or more comments or observations with the two or more case cards to form a theory card.

Another method of forming a case card may generally comprise receiving from a user one or more parameters relating to a treatment performed upon a subject, the one or more parameters including at least an initial condition of the subject prior to a treatment and at least a final condition of the subject upon completion of the treatment, forming an animation which illustrates a change from the initial condition to the final condition based upon the one or more parameters, associating the animation with the one or more parameters within the case card, and displaying the animation within the case card Yet another method of forming a theory card may generally comprise receiving from a user one or more terms relating to a treatment of interest, displaying one or more case cards associated with at least one of the terms, wherein the one or more case cards each comprise one or more parameters relating to the treatment of interest performed upon a subject, the one or more parameters including at least an initial condition of the subject prior to a treatment and at least a final condition of the subject upon completion of the treatment, presenting at least two of the case cards selected for comparison by the user, receiving one or more comments or observations from the user relating to the two or more case cards being compared, and associating the one or more comments or observations with the two or more case cards to form a theory card.

The treatments and products are described in the context of the orthodontic or dental fields particularly with respect to the oral or maxillofacial region. These treatments and products may accordingly relate to the treatment of a subject's dentition, jaws, airways, etc. However, the methods and systems may be applicable to various other fields or conditions, if so desired. For instance, while the exemplary user interfaces display use in the orthodontic field, the methods and systems described for obtaining, displaying, comparing, etc. treatments, as described herein, may be applied in any number of dental or medical fields such as orthopedics, obstetrics, cardiology, urology, ophthalmology, etc.

For example, the user may perform a search using one or more parameters such as keywords relating to a condition of interest. Based on the search parameters, the system may search its database for corresponding parameters and display those results in the form of one or more case cards. An individual case card may generally comprise the file or compilation of information relating to a particular treatment performed on a particular patient and presented in a graphical form that is easily reviewed. Patient-identifying information may be removed from the case card to comply with any patient privacy rules. The treatment information may include parameters such as patient diagnosis, proposed course of treatment, products used, length of treatment, final outcome, etc. Each of the one or more case cards may also include an animation of the patient's dentition showing, e.g., the initial condition at an initial time T1 and the movement, if any, of the patient's teeth to their final position at the end of treatment time T2.

Each of the case cards may be correlated to an individual patient treatment so that a single user may submit a number of different case cards for different (or the same) treatments each for different patients or even the same patient who may have undergone several different treatments. The case cards may also include a number of keywords which provide a readily searchable parameter. The compilation of case cards may in part form a database of searchable treatments and their outcomes.

A user, who may be a practitioner such as an orthodontist or dentist, may upload various parameters of patient treatment data to a remotely located server to create a corresponding case card which summarizes the parameters such as condition (e.g., underbite, overbite, protrusion, crowding, misalignments, etc.) or they may simply utilize the search function. In creating the case card, the uploaded information may be used to create an animation of the patient condition to provide a graphic illustration in the case card of the patient's condition. Moreover, the information provided (e.g., including any images such as 2-D or 3-D x-ray images, fluoroscopic images, etc.) may be used to animate the patient's condition over a period of time such as from a starting condition at an initial period T1 to a final treatment outcome condition at a completion time T2. The animation may be provided to show the patient's progression through each of the treatment steps provided. The creation of the animation may be performed automatically by a processor based on the uploaded information or the animation may be created manually. In either case, the animation may be provided as part of the case card.

With the search yielding one or more relevant case cards and their corresponding animation data, the user may optionally provide a comment, request comments, or create a content comparison between one or more of the presented case cards. The comments or request may then form the basis for a theory or idea card which may be optionally refined by the original user or by other users who may supplement the original comments by providing their own theories, ideas, or comments. The refined theories, ideas, or comments in the refined theory cards may form a final working theory which may be used to match treatment outcomes against initial states, products, or time. Additionally and/or alternatively, the claims may also be evaluated by one or more other users who can review the initial theory cards and refined theory cards and more outcomes may be evaluated to result in a one or more final product cards or industry cards. These product cards may be optionally reviewed by the users or additional users for further discussion and the product cards may be matched with one or more selected key opinion leaders in the field. The product cards may have the added function of allowing a user to purchase directly from the manufacturer on cases where evidence of successful outcomes of treatment are shown.

With the product cards, the best product for treating the initial condition may be optionally identified. This product may include a product used in the treatment or other products which may have been identified by one or more users for alternative treatment options and may include any number of products for use in the orthodontic or dental field, e.g., aligners, brackets, mouthguards, bands, springs, archwires, implants, prostheses, etc. The identified products may be used to form a product card which may allow the user or other users to directly purchase the product featured in the product card or to directly contact the manufacturer of the product. With this product card, other similar products may be searched in the database which utilized either the product or other case cards which also utilized the identified product may be searched and presented to the user.

Generally, the system may be implemented upon a server or computer system and stored upon a non-transitory computer-readable media for access by a central processing unit which may also be in communication with a display. The computer system may be accessible to any number of remotely located electronic devices, e.g., smart phone, computer, tablet, personal digital assistant, etc. which are accessible through a wired or wireless network 38, e.g., WAN, LAN, internet, etc.

Turning now to the creation of the case card, the user may initially create an account on the system through the one or more electronic devices to include user-identifiable information and account access information. Once completed, the user may select one or more patient-specific cases which reside locally, e.g., upon the electronic device. The patient-specific case may include the various parameters relating to the treatment information (with or without the patient-identifying information removed), e.g., patient diagnosis, proposed course of treatment, products used, length of treatment, final outcome, any images such as 2-D or 3-D x-ray images, cone beam computer tomography, MRI, or other inputs, etc. and this treatment information may be electronically formatted in a specified manner so that once the patient information is uploaded electronically to the server or computer system, e.g., through the internet or other transfer protocol, the uploaded patient information may be available for review by the user.

The user may also provide one or more identifiers for the uploaded data or patient information which may be used to facilitate searching of the patient information upon the system. The one or more identifiers may include identifying information such as keywords relating to the patient information. In the orthodontic field, they may also include information relating to the initial positioning of the patient's dentition, positioning of the patient's dentition during treatment, and the final positioning of the patient's dentition. This information may be compiled by the system and used to create the animation to illustrate the movement of the patient's dentition, e.g., from an initial positioning of the dentition at an initial period of time T1 to the final positioning of the dentition at the end of treatment at time T2 that the user may selectively advance and/or rewind. The presentation of the animation within the case card may provide for an enhanced understanding of the treatment applied, the effects of treatment on the patient's dentition, and the final outcome of the treatment.

Once the one or more identifiers have been completed and reviewed, the user may publish the uploaded patient information into a completed case card which is available for searching and display by other users. The case card may be published either with or without the animation and in the case of publication without the animation, the animation may be incorporated into the published case card once the animation has been completed. Alternatively, the animation may be omitted although it is desirable to incorporate the animation with the case card.

After the user has created an account on the system, the user may optionally create one or more case cards for inclusion into the database of case cards. Alternatively, the user may opt for simply searching for case cards with treatments for a condition of interest to the user.

In another variation, after the user has created an account and optionally created one or more case cards, as described herein, the user may perform a search for case cards relating to a treatment of interest. The user may review one or more of the relevant case cards and create a queue of case cards for comparison. Based on the user's review, the user may provide one or more comments or observations regarding the comparison between one or more of the case cards. The comments or observations may form the basis of a theory card which may be stored in the memory of the system. The user may repeat the search for additional case cards to include into the user's queue as many times as desired for further comments or observations. Once the user has completed any comments or observations regarding the comparison between the case cards, the user may choose to publish these comments or observations in the form of a theory card, which may become available on the database for searching and review by other users.

In yet another variation, the user may create one or more theory cards, as described, but the user may also optionally solicit additional comments or observations from one or more selected third parties. The user may solicit one or more third-parties for their own comments or observations regarding the comparison shown in the theory card created by the user by contacting the one or more third-parties through the system. The one or more third parties may choose to ignore or accept the solicitation, but upon accepting the solicitation, the third party may perform their own search for additional case cards, e.g., to confirm, refute, or comment on the theory card provided by the initial user. These additional case cards may be added to the initial user's queue along with any additional comments or observations from the third-party.

Because treatments, comments, and observations may involve any number of different products, as described herein with respect to the product card, after the user has created an account and performed a search for case cards of interest, as described herein, the user may review any of the products used in the case cards of interest to create a produce card. The user may select the product of interest upon which a search may be performed automatically for other case cards which have also used the same product or other products that may be of interest to the user. The user may optionally contact a manufacturer which produces one or more of the products of interest through the system.

DETAILED DESCRIPTION OF THE INVENTION

Figure 1A:
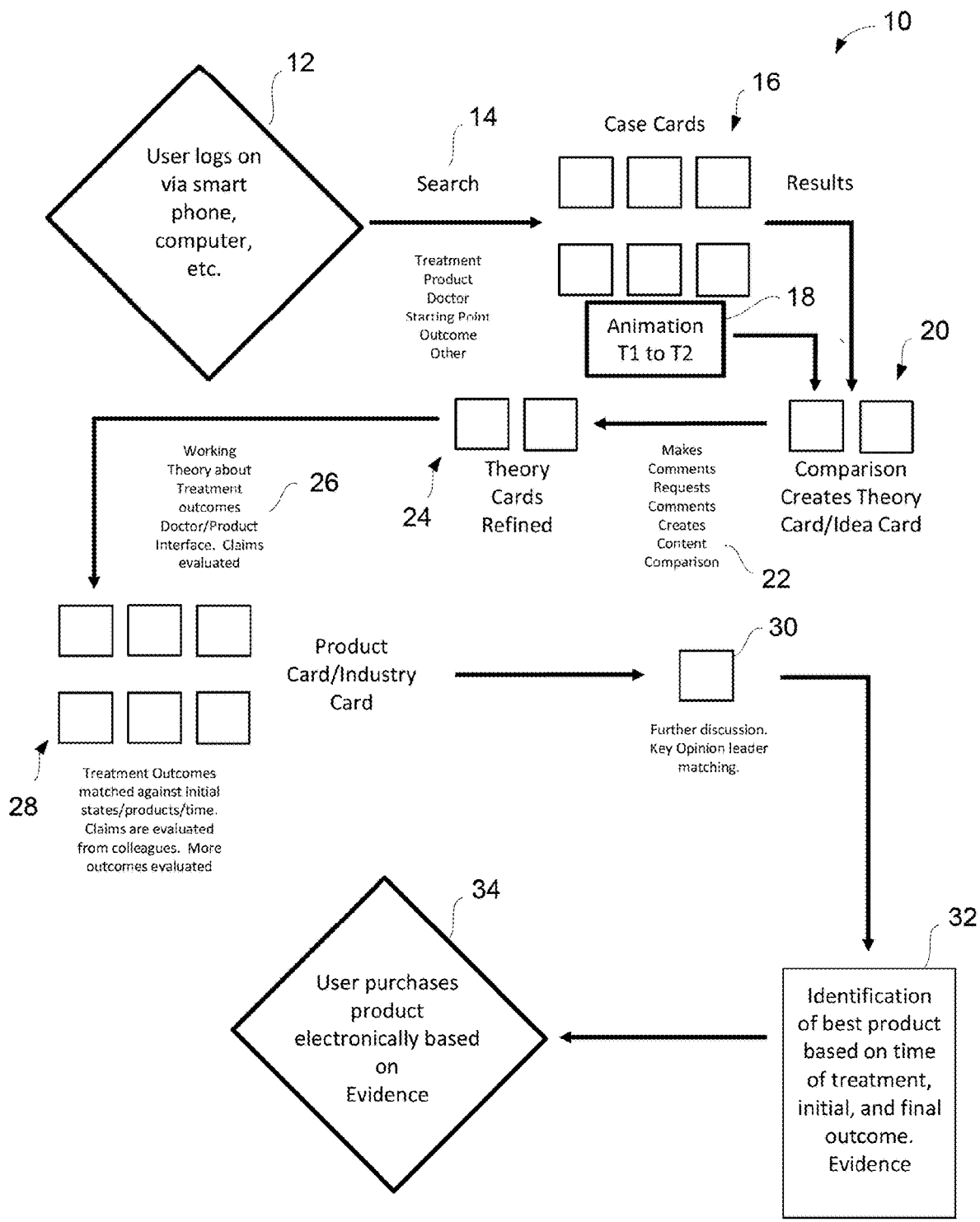
FIG. 1A shows a representative flow diagram of one variation of a system which allows for a user to create one or more case cards for comparison to other treatments performed by other users.

In one variation of the system 10, as shown in the schematic diagram of FIG. 1A, users may access a remote server through any number of electronic devices, e.g., smart phone, computer, tablet, personal digital assistant, etc. 12 to conduct any number of searches 14 for related treatments of interest, use of products during treatments, one or more particular doctors, condition of a patient at a starting point, resulting outcome from treatments, or any other number of conditions or features.

The treatments and products are described in the context of the orthodontic or dental fields particularly with respect to the oral or maxillofacial region. These treatments and products may accordingly relate to the treatment of a subject's dentition, jaws, airways, etc. However, the methods and systems may be applicable to any number of various other fields or conditions, if so desired. For instance, while the exemplary user interfaces display use in the orthodontic field, the methods and systems described for obtaining, displaying, comparing, etc. treatments, as described herein, may be applied in any number of dental or medical fields such as orthopedics, obstetrics, cardiology, urology, ophthalmology, etc.

For example, the user may perform a search 14 using one or more parameters such as keywords relating to a condition of interest. Based on the search parameters, the system may search its database for corresponding parameters and display those results in the form of one or more case cards 16. An individual case card 16 may generally comprise the file or compilation of information relating to a particular treatment performed on a particular patient and presented in a graphical form that is easily reviewed. Patient-identifying information may be removed from the case card 16 to comply with any patient privacy rules. The treatment information may include parameters such as patient diagnosis, proposed course of treatment, products used, length of treatment, final outcome, etc. Each of the one or more case cards 16 may also include an animation 18 of the patient's dentition showing, e.g., the initial condition at an initial time T1 and the movement, if any, of the patient's teeth to their final position at the end of treatment time T2.

Each of the case cards 16 may be correlated to an individual patient treatment so that a single user may submit a number of different case cards 16 for different (or the same) treatments each for different patients or even the same patient who may have undergone several different treatments. The case cards 16 may also include a number of keywords which provide a readily searchable parameter. The compilation of case cards 16 may in part form a database of searchable treatments and their outcomes.

A user, who may be a practitioner such as an orthodontist or dentist, may upload various parameters of patient treatment data to a remotely located server to create a corresponding case card 16 which summarizes the parameters such as condition (e.g., underbite, overbite, protrusion, crowding, misalignments, etc.) or they may simply utilize the search function 14. In creating the case card 16, the uploaded information may be used to create an animation of the patient condition to provide a graphic illustration in the case card 16 of the patient's condition. Moreover, the information provided (e.g., including any images such as 2-D or 3-D x-ray images, fluoroscopic images, etc.) may be used to animate 18 the patient's condition over a period of time such as from a starting condition at an initial period T1 to a final treatment outcome condition at a completion time T2. The animation 18 may be provided to show the patient's progression through each of the treatment steps provided. The creation of the animation may be performed automatically by a processor based on the uploaded information or the animation may be created manually. In either case, the animation may be provided as part of the case card 16.

With the search 14 yielding one or more relevant case cards 16 and their corresponding animation 18 data, the user may optionally provide a comment, request comments, or create a content comparison 22 between one or more of the presented case cards 16. The comments or request may then form the basis for a theory or idea card 20 which may be optionally refined 24 by the original user or by other users who may supplement the original comments by providing their own theories, ideas, or comments. The refined theories, ideas, or comments in the refined theory cards 24 may form a final working theory 26 which may be used to match treatment outcomes against initial states, products, or time.

Additionally and/or alternatively, the claims may also be evaluated by one or more other users who can review the initial theory cards 20 and refined theory cards 24 and more outcomes may be evaluated to result in a one or more final product cards or industry cards 28. These product cards 28 may be optionally reviewed by the users or additional users for further discussion 30 and the product cards may be matched with one or more selected key opinion leaders in the field.

With the product cards 28, the best product for treating the initial condition may be optionally identified. This product may include a product used in the treatment or other products which may have been identified by one or more users for alternative treatment options and may include any number of products for use in the orthodontic or dental field, e.g., aligners, brackets, mouthguards, bands, springs, archwires, implants, prostheses, etc. The identified products may be used to form a product card 32 which may allow the user or other users to directly purchase 34 the product featured in the product card 32 or to directly contact the manufacturer of the product. With this product card 34, other similar products may be searched in the database which utilized either the product or other case cards which also utilized the identified product may be searched and presented to the user.

Figure 1B:
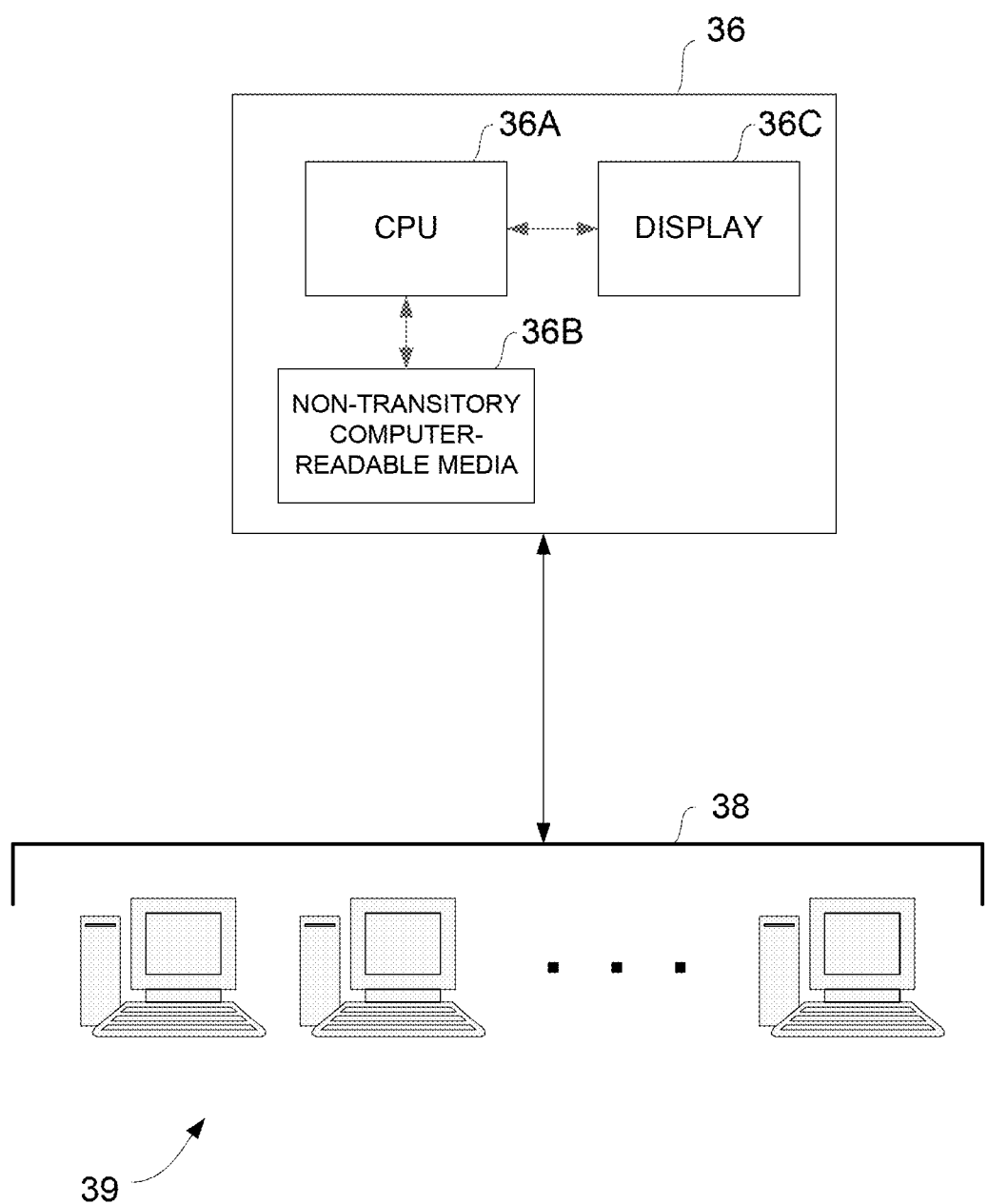
FIG. 1B shows a representation of how the system may be implemented over a network with other users.

Generally, the system may be implemented upon a server or computer system 36 and stored upon a non-transitory computer-readable media 36B for access by a central processing unit 36A which may also be in communication with a display 36C, as shown in FIG. 1B. The computer system 36 may be accessible to any number of remotely located electronic devices 39, e.g., smart phone, computer, tablet, personal digital assistant, etc. which are accessible through a wired or wireless network 38, e.g., WAN, LAN, internet, etc.

Figure 2:
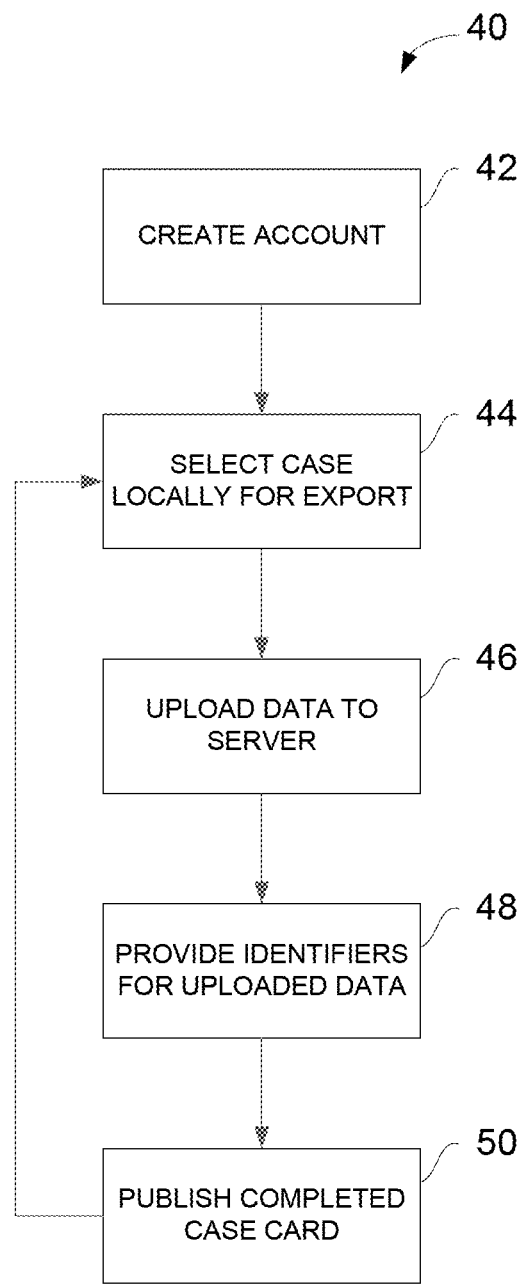
FIG. 2 shows a flow diagram illustrating the creation of a case card for a particular treatment.

Turning now to the creation of the case card, FIG. 2 shows a flow diagram 40 illustrating how the case card may be created. The user may initially create an account 42 on the system through the one or more electronic devices 39 to include user-identifiable information and account access information. Once completed, the user may select one or more patient-specific cases which reside locally, e.g., upon the electronic device. The patient-specific case may include the various parameters relating to the treatment information (with or without the patient-identifying information removed), e.g., patient diagnosis, proposed course of treatment, products used, length of treatment, final outcome, any images such as 2-D or 3-D x-ray images, fluoroscopic images, etc. and this treatment information may be electronically formatted in a specified manner so that once the patient information is uploaded 46 electronically to the server or computer system 36, e.g., through the internet or other transfer protocol, the uploaded patient information may be available for review by the user.

The user may also provide one or more identifiers for the uploaded data or patient information 48 which may be used to facilitate searching of the patient information upon the system. The one or more identifiers may include identifying information such as keywords relating to the patient information. In the orthodontic field, they may also include information relating to the initial positioning of the patient's dentition, positioning of the patient's dentition during treatment, and the final positioning of the patient's dentition. This information may be compiled by the system and used to create the animation 18 to illustrate the movement of the patient's dentition, e.g., from an initial positioning of the dentition at an initial period of time T1 to the final positioning of the dentition at the end of treatment at time T2 that the user may selectively advance and/or rewind. The presentation of the animation 18 within the case card may provide for an enhanced understanding of the treatment applied, the effects of treatment on the patient's dentition, and the final outcome of the treatment.

Once the one or more identifiers 48 have been completed and reviewed, the user may publish the uploaded patient information into a completed case card 50 which is available for searching and display by other users. The case card 50 may be published either with or without the animation 18 and in the case of publication without the animation, the animation 18 may be incorporated into the published case card 50 once the animation has been completed. Alternatively, the animation 18 may be omitted although it is desirable to incorporate the animation 18 with the case card 50.

Figure 3A:
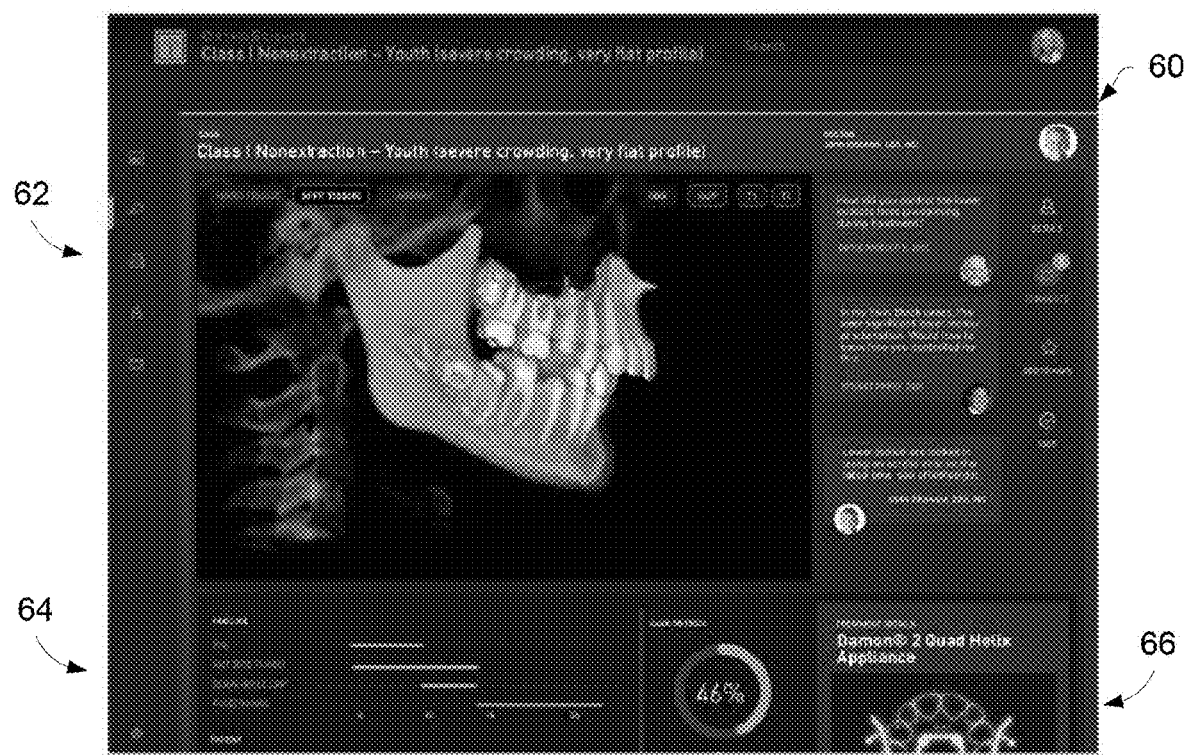
FIGS. 3A and 3B show representative user interfaces for a particular case card.
Figure 3B:

FIGS. 3A and 3B illustrate an example of a graphical interface of a complete case card 60 which may be presented to the user. The case card 60 may show the practitioner who treated the condition and an image of the animation 62 may also be shown to illustrate the movement of the patient's dentition from a starting condition with any intermediate steps to a final corrected condition. The timeline 64 over which the treatment occurred may also be illustrated as well as any specific products 66 (as described herein) which were used to effect the treatment. Manufacturer information for the specific product 66 may also be optionally included. Any additional notes 68 provided by the treating practitioner may also be included. When a search is performed by a user, a number of relevant case cards may be presented based on the search results from the database. The user may select a particular case card for display and review but a listing of additional case cards 70 relevant to the search inquiry may also be presented for case comparison by the user.

Figure 3C:
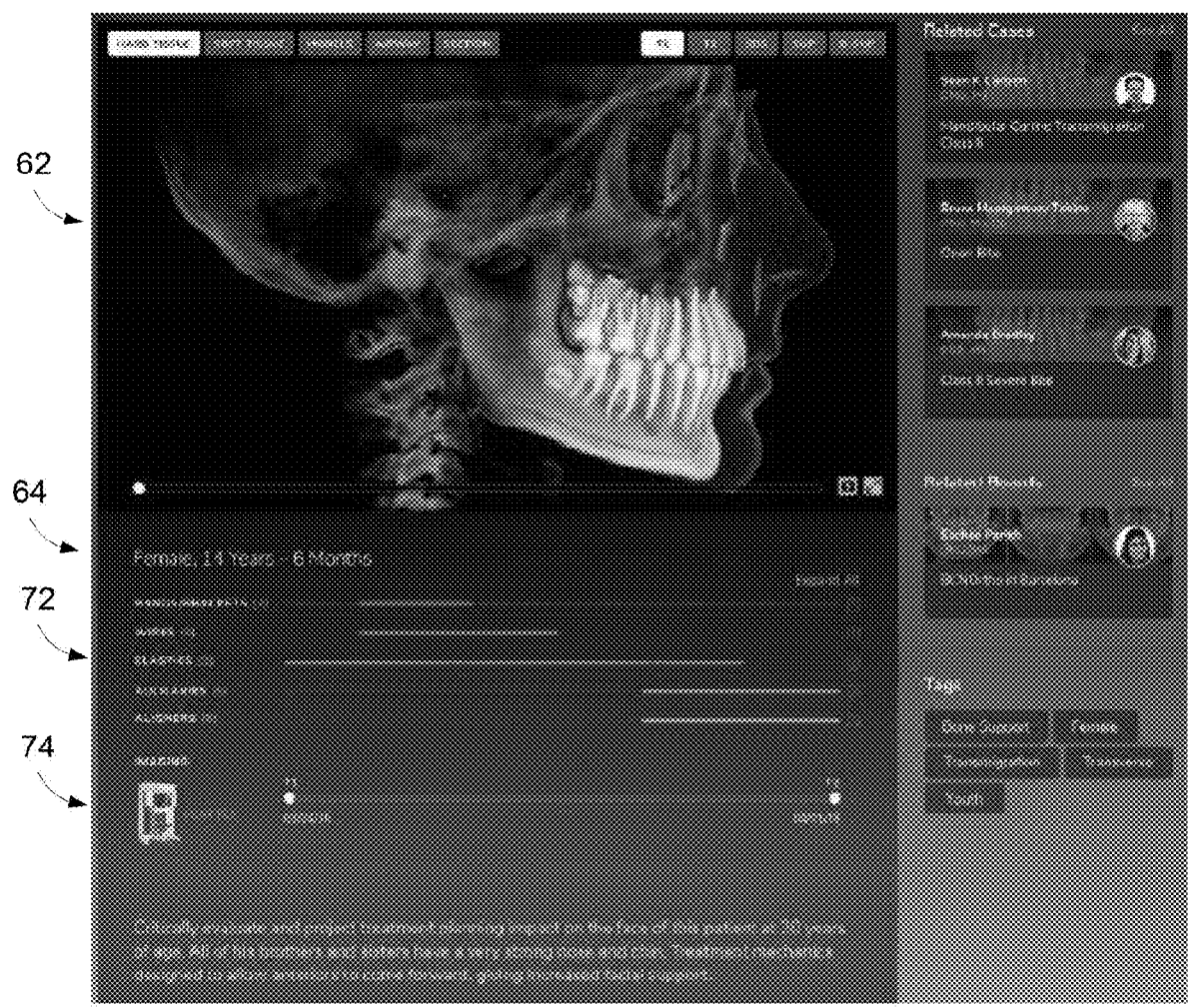
FIGS. 3C and 3D show representative user interfaces for displaying treatment timelines.

The timeline 64 shown may be used to display information such as when particular appliances or treatments were applied over the course of treatment. In the example shown in FIG. 3C, the timeline 64 shown may display a time scale 74 which can be implemented as a graphical slider interface beginning from an initial time T1 (e.g., just prior to or at the beginning of treatment) and extending to a completion time T2 (e.g., at treatment completion or post treatment). One or more different treatments 72 may be indicated over the timeline 74 and correlated to when a particular treatment was started and when it was completed. Hence, any number of treatments may be indicated and correlated and can instantly display which appliances were used and when they were applied. The example shown illustrates how elastics were initially applied with the subsequent application of bands/brackets and wires and the eventual removal of the elastics with the application of aligners to complete the treatment at the completion time T2.

As noted, the time scale 74 may function as a graphical slider interface which is correlated to when the one or more treatments 72 were applied as well as being correlated to the animation 62 which may illustrate the progression of the treatment over the course of time. Thus, the time scale 74 may be positioned by a user to any intermediate position over the timeline 64 to display a position of the dentition which is correlated to the appliance or treatment being applied at that selected time.

The relevant information (e.g., dates of appliance application, treatment dates and times, resulting position of the dentition, type of appliance, etc.) pertaining to the timeline 64 of when particular treatments 72 were applied may be obtained from the patient information that is uploaded 46 electronically to the server or computer system 36, as discussed herein. This relevant information may be extracted from the patient information either manually or automatically by the computer system 36 so that the timeline 64 may be constructed accordingly.

Figure 3D:
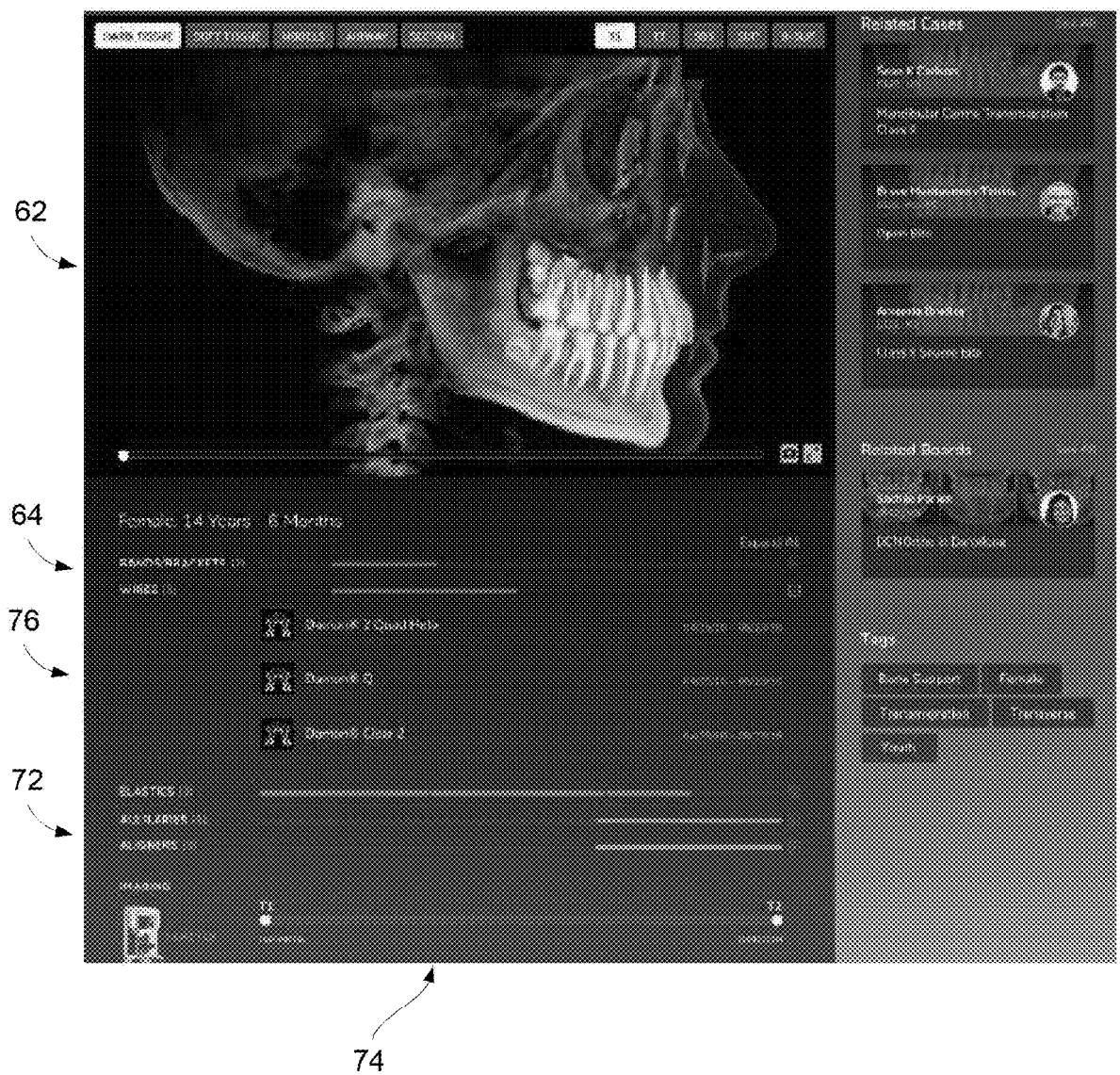

Additionally, because the relevant information obtained from the patient information may include the type or types of particular appliances utilized in a particular treatment 72, the timeline 64 may be programmed to also optionally display the actual appliance or product used. This allows a user to select any one of the particular treatments 72 to instruct the computer system 36 to further display the one or more actual appliance or product used 76, as shown in FIG. 3D. With this appliance information displayed, the user may also optionally select any one of the individual appliances to obtain detail information about the appliance, the manufacturer, and/or the appliance ordering information.

Figure 3E:
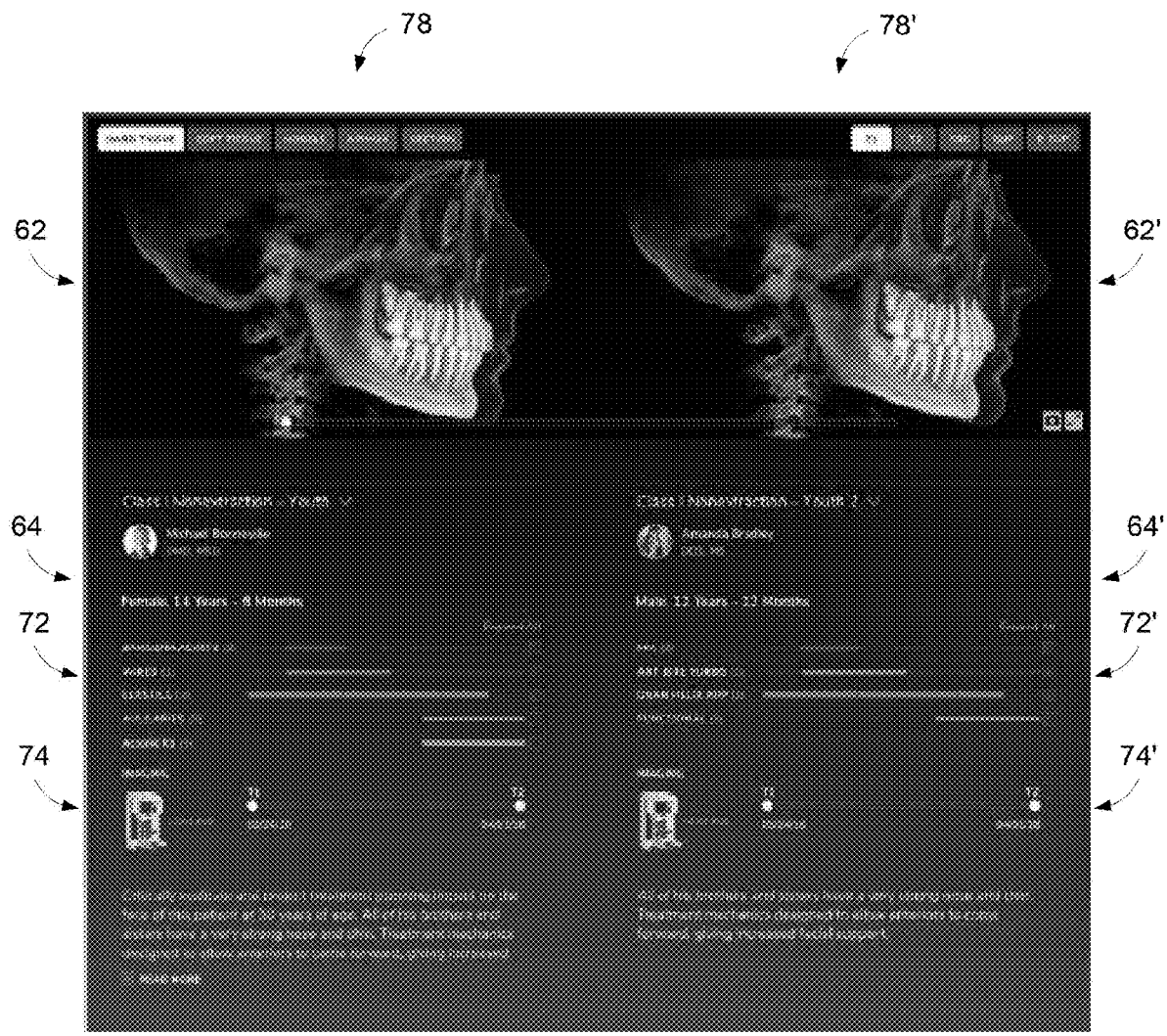
FIG. 3E shows a representative user interface for displaying one or more treatment timelines for comparison.

Yet another optional feature may include the ability to display one or more treatments 78, 78' side-by-side, as shown in FIG. 3E, so that a comparison of the respective timelines 64, 64', the one or more treatments 72, 72', the time scales 74, 74', and the corresponding animations 62, 62' may be displayed for comparison purposes. Depending on the length of the treatment, adjusting the time scale from one treatment 78 may be correlated to the comparable time scale of the compared treatment 78' so that the user may view and compare the treatments and their results.

Figure 4:
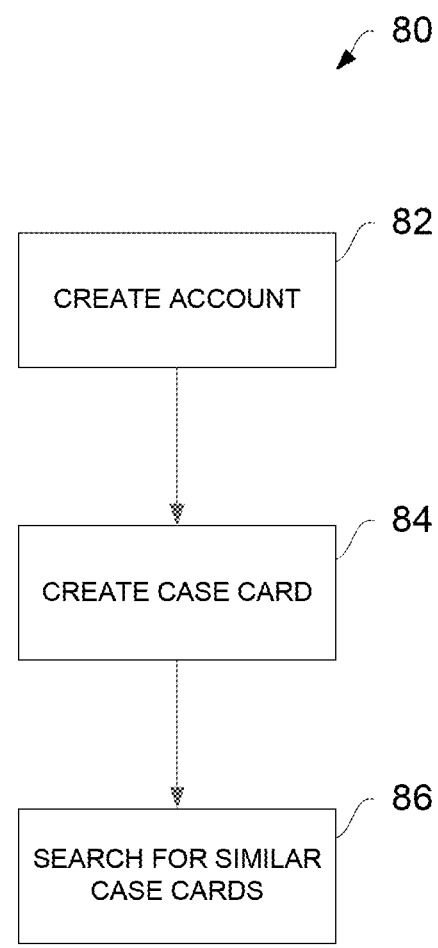
FIG. 4 shows a flow diagram illustrating one variation for utilizing the case cards in searching for similar treatments or conditions.
Figure 5A:
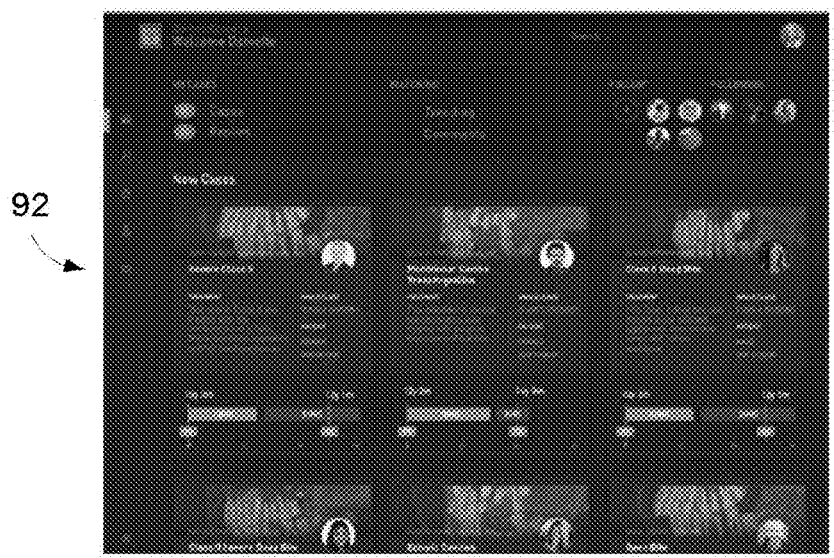
FIGS. 5A to 5C show representative examples of a user interface designed to allow for a user to search for various case cards and display the relevant case cards.
Figure 5B:
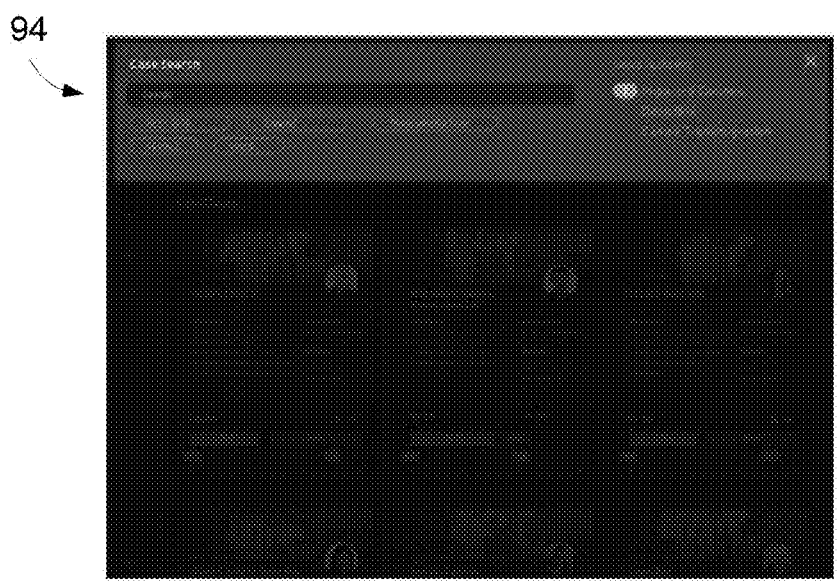
Figure 5C:
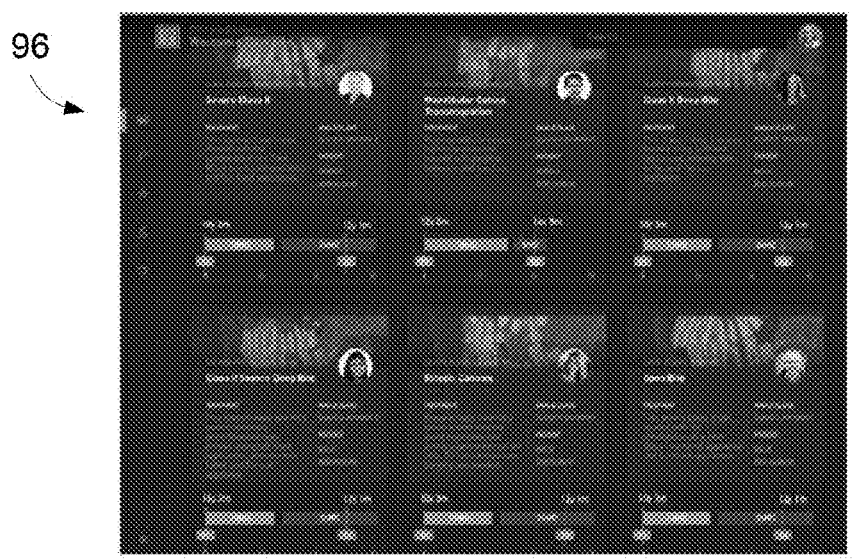

FIG. 4 shows a flow diagram 80 illustrating an example of how a user may search for case cards of interest. After the user has created an account 82 on the system, the user may optionally create one or more case cards 84 for inclusion into the database of case cards. Alternatively, the user may opt for simply searching for case cards 86 with treatments for a condition of interest to the user. For instance, FIGS. 5A to 5C illustrate an example of a graphical interface 90 where the user may initially log into the system upon which a number of case cards 92, e.g., newly uploaded case cards, may be displayed. The user may enter one or more keywords into a search feature 94, as shown in the user interface in FIG. 5B, and the system may query the database and present one or more case cards of interest 96, as shown in FIG. 5C, for selection and review by the user.

Figure 6:
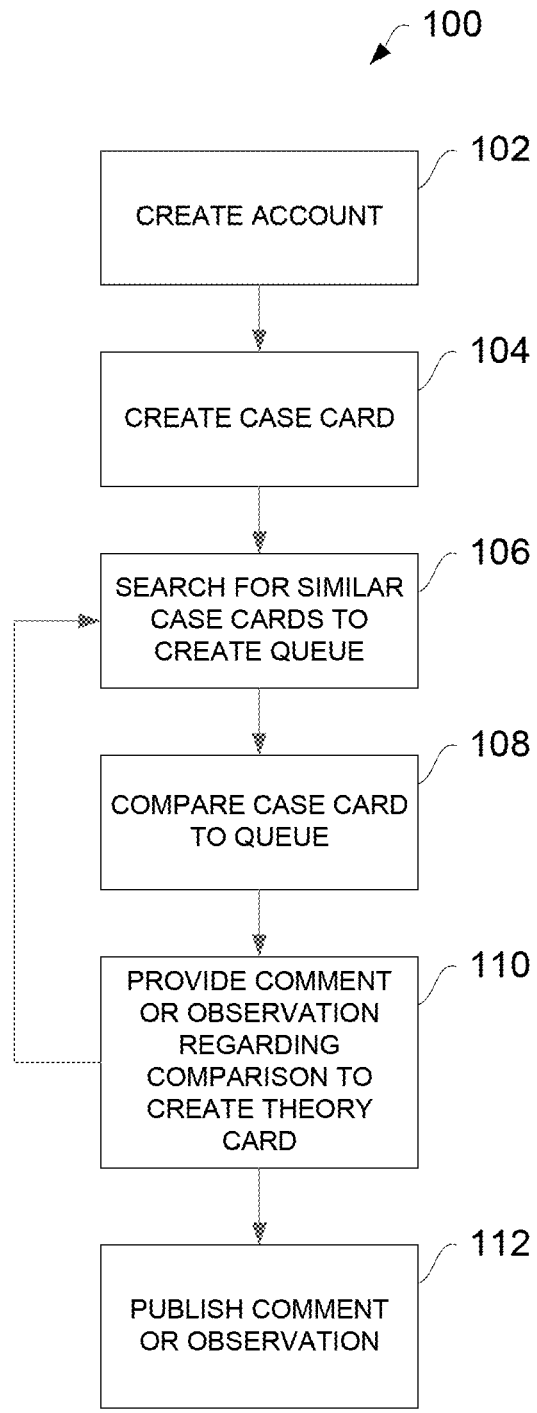
FIG. 6 shows a flow diagram of illustrating how a user may create a theory card based on a comparison with other case cards.

In another variation, FIG. 6 illustrates a flow diagram 100 in which the user may optionally create a theory card. After the user has created an account 102 and optionally created one or more case cards 104, as described above, the user may perform a search for case cards relating to a treatment of interest 106. The user may review one or more of the relevant case cards and create a queue 106 of case cards for comparison 108. Based on the user's review, the user may provide one or more comments or observations regarding the comparison between one or more of the case cards. The comments or observations may form the basis of a theory card 110 which may be stored in the memory of the system. The user may repeat the search for additional case cards to include into the user's queue as many times as desired for further comments or observations. Once the user has completed any comments or observations regarding the comparison between the case cards, the user may choose to publish these comments or observations 112 in the form of a theory card, which may become available on the database for searching and review by other users.

Figure 7:
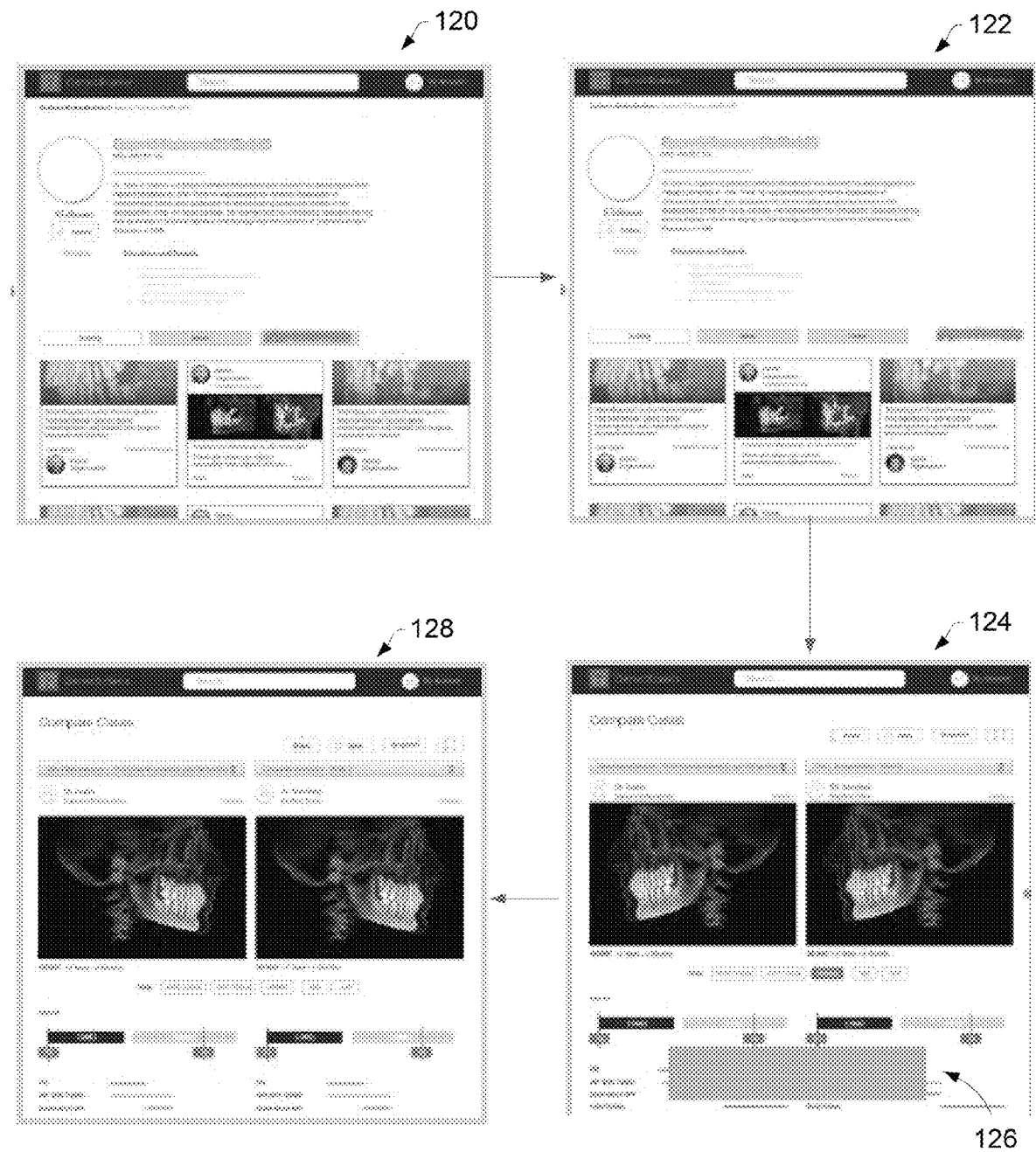
FIG. 7 shows representative examples of a user interface for creating a theory card.

FIG. 7 illustrates a graphical interface to show one example of how a theory card may be created by a user. As shown by the graphical interface 120, the user may perform a search on the system to find case cards which the user may have created or that other users may be created. Once the user finds at least two cards of interest, the user may choose to compare the two case cards 122 upon which the relevant case cards may be displayed for comparison 124 and for entry of the user's comments or observations 126. The user may also select the appropriate images between the animations of each case card to highlight or support the user's comments or observations 126 and once completed, the user may publish the comparison as a theory card 128 which may then become available as a searchable item for review by other users.

Figure 8:
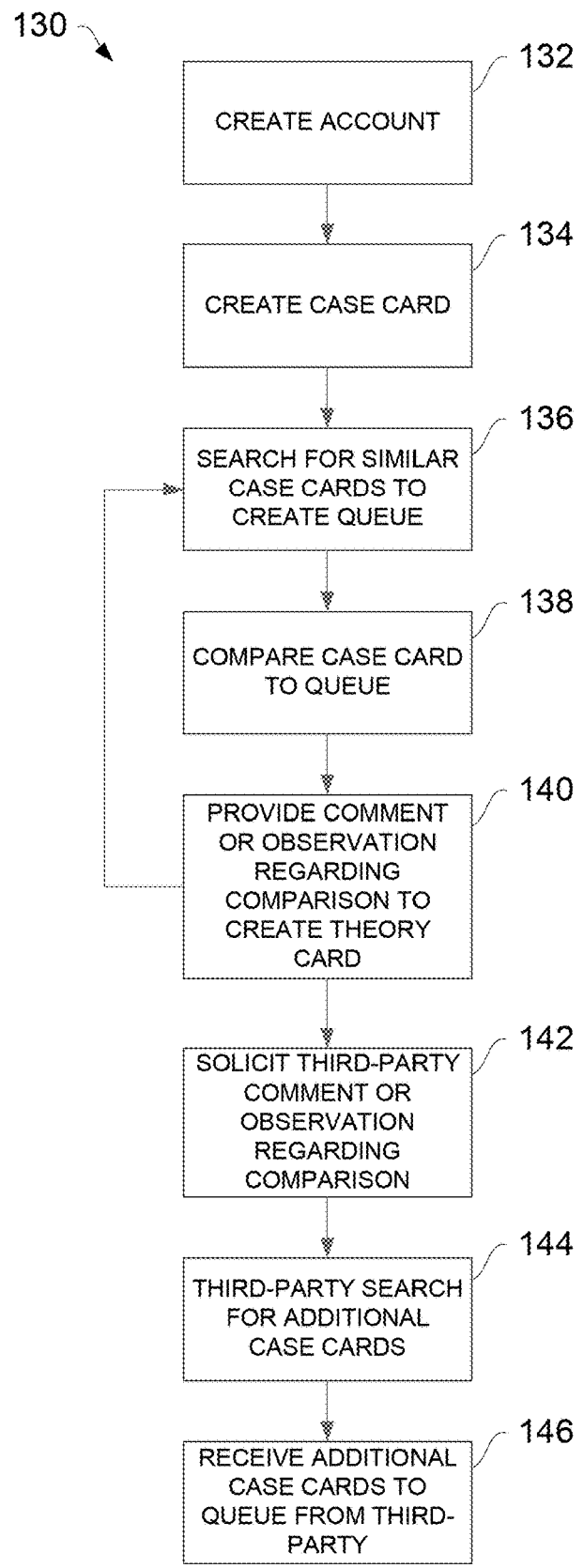
FIG. 8 shows a flow diagram illustrating how the user may interact with other users with theory cards.

In yet another variation, the user may create one or more theory cards, as previously described, but the user may also optionally solicit additional comments or observations from one or more selected third parties. FIG. 8 shows a flow diagram 130 illustrating how the user, after creating an account 132, optionally creating one or more case cards 134, performing a search for other similar case cards 136, comparing the case cards 138, and providing one or more comments or observations 140 to create a theory card, as described herein.

The user may then solicit one or more third-parties for their own comments or observations regarding the comparison shown in the theory card created by the user 142 by contacting the one or more third-parties through the system. The one or more third parties may choose to ignore or accept the solicitation, but upon accepting the solicitation, the third party may perform their own search for additional case cards 144, e.g., to confirm, refute, or comment on the theory card provided by the initial user. These additional case cards may be added to the initial user's queue 146 along with any additional comments or observations from the third-party.

Figure 9:
FIG. 9 shows representative examples of a user interface for interacting with other users with theory cards.

FIG. 9 shows one example of a graphical interface illustrating how a user may solicit one or more third-parties. After the user has logged into the system 150 and performed a search 152 of relevant case cards and entered any comments or observations 154 with respect to a comparison between two case cards, the user may publish their theory card 156, as described herein. The user may then optionally select one or more third-parties, e.g., the creator of one of the case cards of interest, and send them a solicitation 158 directly through the system. The third-party may choose to ignore or accept the solicitation but if the solicitation is accepted, the third-party may review the theory card 156 and the comments and observations from the initial user.

The third-party may optionally respond with any additional comments or observations. Alternatively, the third-party may perform their own search 162 for other case cards and select one or more from the search results for additional comparisons 164. The third-party may then provide any additional comments or observations 166 to create a new theory card or add to the initial theory card for review by the initial user 168.

Figure 10:
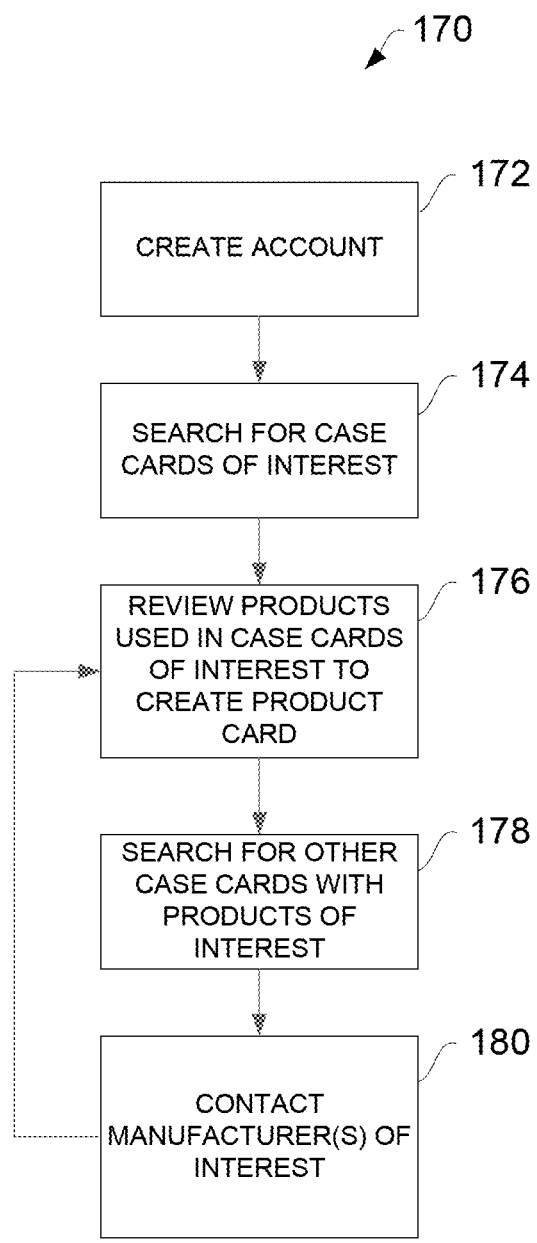
FIG. 10 shows a flow diagram illustrating how the user may create a product card.

Because treatments, comments, and observations may involve any number of different products, as described herein with respect to product card 32, FIG. 10 illustrates an example of a flow diagram 170 for creating such a product card. After the user has created an account 172 and performed a search for case cards of interest 174, as described herein, the user may review any of the products used in the case cards of interest to create a product card 176. The user may select the product of interest upon which a search may be performed automatically for other case cards which have also used the same product or other products that may be of interest to the user 178. The user may optionally contact a manufacturer which produces one or more of the products of interest 180 through the system.

Figure 11A:
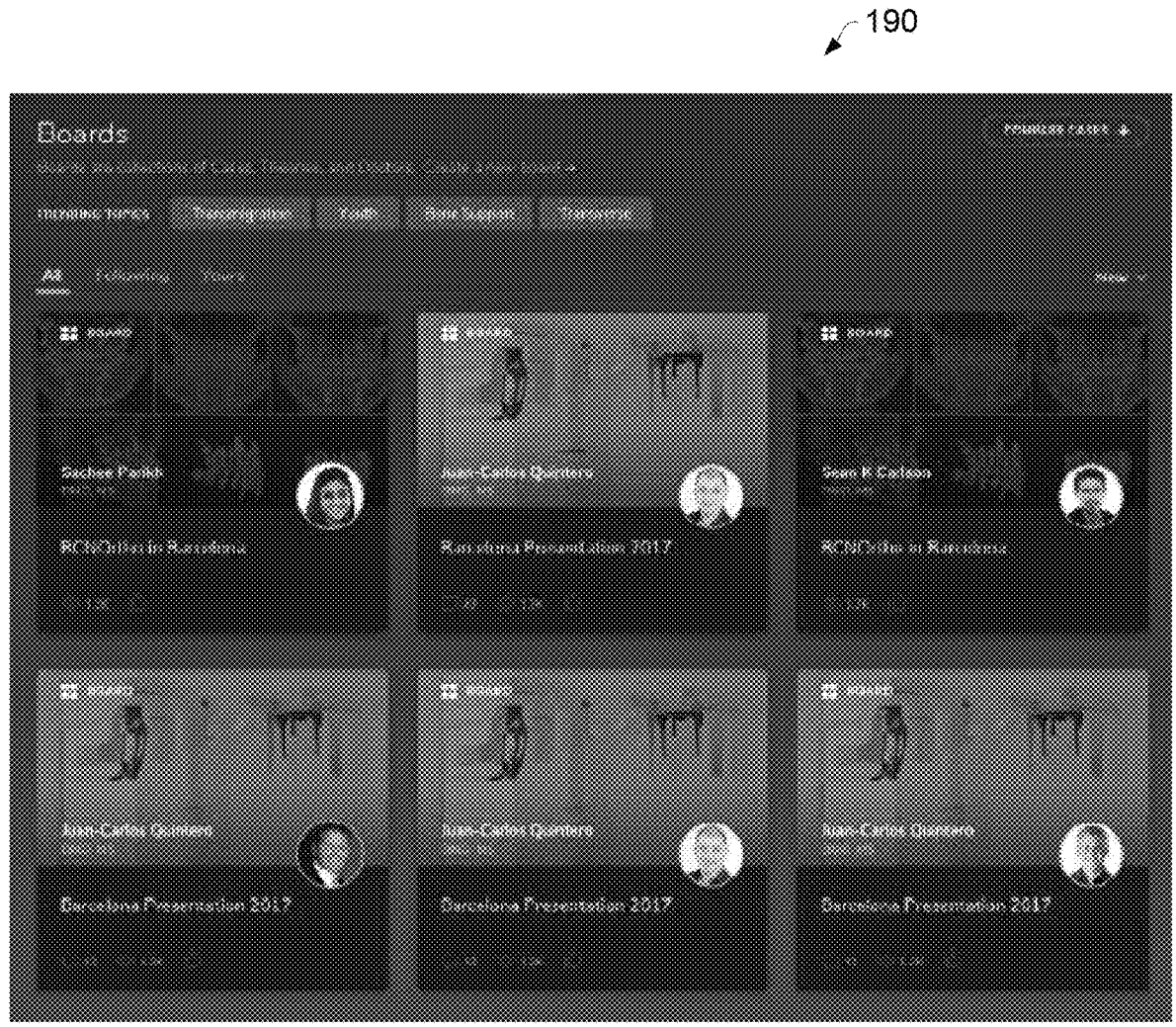
FIG. 11A shows a representative user interface of a board display.

Yet another feature available to a user may include a board display 190, as shown in the example of FIG. 11A. The board display 190 may include a display of any selected cards (such as case cards, theory cards, product cards, etc.) or any other generated notes, observations, comments, etc. that a user may select for display in a user interface. The displayed cards, for instance, may function as a repository for the user who may organize the information in any manner so desired. Moreover, the selected information on the board display 190 may be maintained in a private setting or shared with one or more other users on the network 38.

Figure 11B:
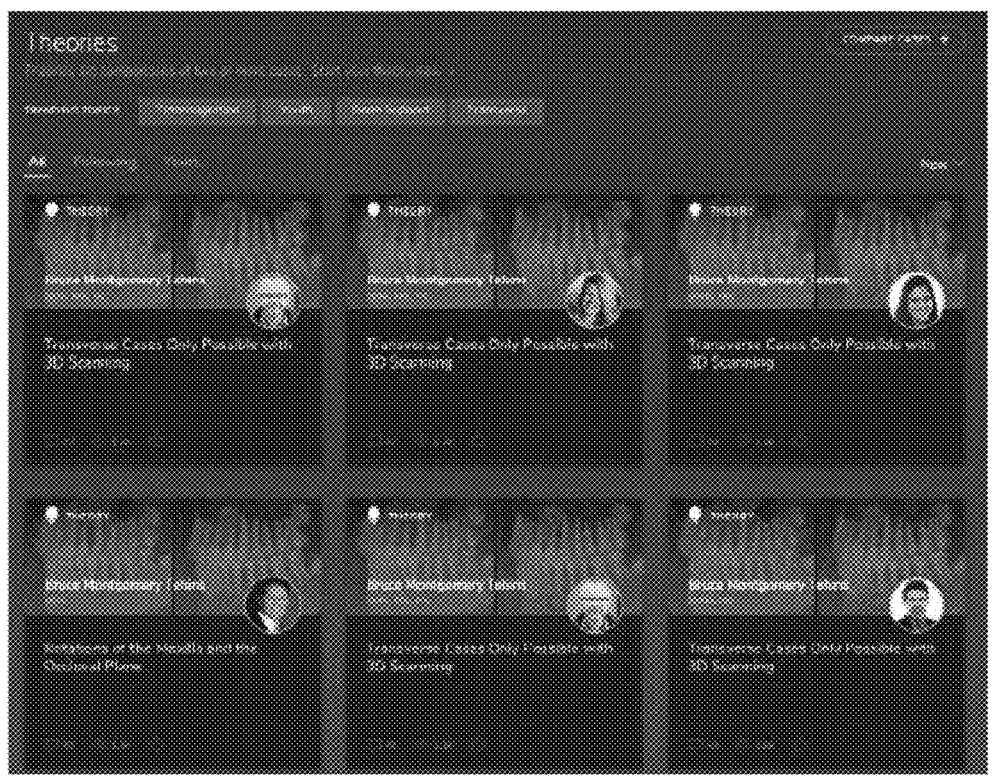
FIGS. 11B and 11C show representative user interfaces of board displays organized around one or more topics of interest.
Figure 11C:
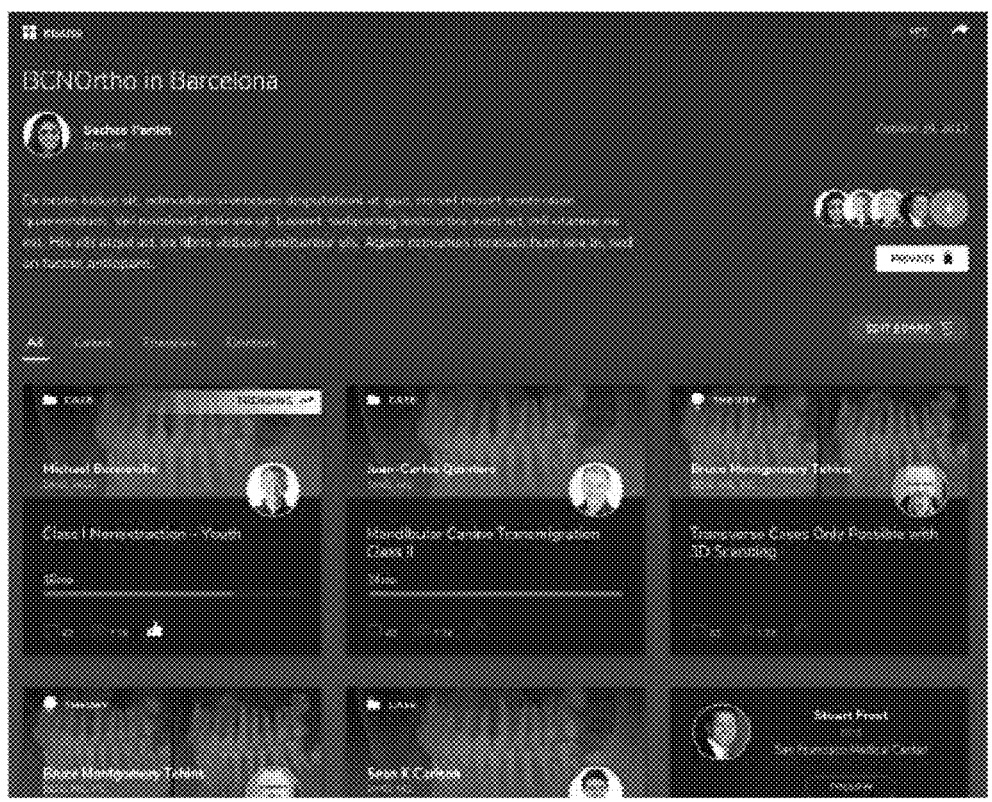

Because of the flexibility in organizing the information on a board display 190, the user may create particular boards organized by any number of topics. For instance, the user may create a board display 192 organized by one or more particular theories, as shown in FIG. 11B, or a board display 194 organized around particular events, as shown in FIG. 11C, or any other topic of interest.

The applications of the devices and methods discussed above are not limited to the fields of orthodontics or dentistry but may include any number of further applications in other fields. Modification of the above-described assemblies and methods for carrying out the invention, combinations between different variations as practicable, and variations of aspects of the invention that are obvious to those of skill in the art are intended to be within the scope of the claims.

What is claimed is:

1. A computer-implemented method of forming a case card, comprising: receiving from a user via a network one or more parameters relating to a treatment and to treatment-related information previously performed upon an oral or maxillofacial region of a subject, the one or more parameters including at least an initial position of the oral or maxillofacial region prior to a treatment and at least a final position of the oral or maxillofacial region upon completion of the treatment; associating one or more keyword searchable parameters with the treatment previously performed such that the case card is electronically retrievable via the network by another user not associated with the treatment previously performed; forming an animation which illustrates a movement of the oral or maxillofacial region from the initial position to the final position based upon the one or more parameters; associating the animation with the one or more parameters within the case card; displaying the animation within the case card; displaying a timeline of the treatment applied over a course of the treatment such that the animation is displayed within a first region of the case card and the timeline is displayed within a second region of the case card in proximity to the first region, wherein the timeline is correlated to a progression of the treatment from the initial position to the final position such that the timeline is manipulatable by the user to display one or more intermediate positions of the oral or maxillofacial region, and wherein the treatment-related information includes at least treatment time and appliance type which were used in the treatment such that the timeline is further correlated to display the appliance type used at a selected treatment time during the progression of the treatment with detail information about the appliance including a manufacturer of the appliance type; and displaying in the case card to the user, wherein the case card provides a contact to the manufacturer which is contacted by the user directly through the network via the case card.

2. The method of claim 1 wherein receiving from a user via a network comprises receiving the one or more parameters to a computer system via the network.

3. The method of claim 1 wherein forming an animation comprises forming the animation from one or more images of the oral or maxillofacial region at least in the initial position and the final position.

4. The method of claim 3 wherein displaying the animation comprises displaying one or more intermediate positions of the oral or maxillofacial region.

5. The method of claim 1 wherein associating the animation further comprises associating one or more keywords with the case card, wherein the one or more keywords relate to the treatment.

6. The method of claim 1 wherein associating the animation further comprises associating one or more additional treatments applied to the subject with the animation.

7. The method of claim 1 wherein displaying a timeline comprises displaying the timeline of the one or more additional treatments applied over a course of the treatment.

8. The method of claim 6 further comprising displaying the animation at one or more intermediate positions correlated to the one or more additional treatments.

9. The method of claim 1 further comprising displaying the case card with one or more additional case cards under one or more selected topics.

10. A system, comprising: a non-transitory computer readable medium for storing computer readable program code; and a processor in communication with the non-transitory computer readable medium, the processor being configured to perform operations including: receiving via a network one or more parameters relating to a treatment and to treatment-related information previously performed upon an oral or maxillofacial region of a subject, the one or more parameters including at least an initial position of the oral or maxillofacial region prior to a treatment and at least a final position of the oral or maxillofacial region upon completion of the treatment to form a case card; associating one or more keyword searchable parameters with the treatment previously performed such that the case card is electronically retrievable via the network by another user not associated with the treatment previously performed; associating an animation with the one or more parameters within the case card, wherein the animation illustrates a movement of the oral or maxillofacial region from the initial position to the final position based upon the one or more parameters; displaying the animation within the case card; and displaying a timeline of the treatment applied over a course of the treatment such that the animation is displayed within a first region of the case card and the timeline is displayed within a second region of the case card in proximity to the first region, wherein the timeline is correlated to a progression of the treatment from the initial position to the final position such that the timeline is manipulatable by the user to display one or more intermediate positions of the oral or maxillofacial region, and wherein the treatment-related information includes at least treatment time and appliance type which were used in the treatment such that the timeline is further correlated to display the appliance type used at a selected treatment time during the progression of the treatment with detail information about the appliance including a manufacturer of the appliance type, and displaying in the case card to the user, wherein the case card provides a contact to the manufacturer which is contacted by the user directly through the network via the case card.

11. The system of claim 10 wherein the processor is in communication with one or more electronic devices via the network.

12. The system of claim 10 wherein the one or more parameters further include treatment-related information.

13. The system of claim 12 wherein the treatment-related information includes at least treatment time and product type.

14. The system of claim 10 wherein the animation is comprised of one or more images of the dentition at least in the initial position and the final position.

15. The system of claim 10 wherein associating the animation further comprises associating one or more keywords with the case card, wherein the one or more keywords relate to the treatment.

16. The system of claim 10 wherein associating the animation further comprises associating one or more additional treatments applied to the subject with the animation.

17. The system of claim 10 wherein displaying a timeline comprises displaying the timeline of the one or more additional treatments applied over a course of the treatment.

18. The system of claim 16 further comprising displaying the animation at one or more intermediate positions correlated to the one or more additional treatments.

19. The system of claim 10 further comprising displaying the case card with one or more additional case cards under one or more selected topics.

20. A computer-implemented method of forming a theory card, comprising: receiving from a user via a network one or more keyword searchable terms relating to a treatment of interest and to treatment-related information previously performed upon an oral or maxillofacial region of a subject; displaying one or more case cards formed by at least one other user and associated with at least one of the keyword searchable terms such that the one or more case cards are electronically retrieved via the network by the user not associated with the treatment previously performed, wherein the one or more case cards each comprise one or more parameters relating to the treatment of interest, the one or more parameters including at least an initial position of the oral or maxillofacial region prior to a treatment and at least a final position of the oral or maxillofacial region upon completion of the treatment, and wherein the treatment-related information includes at least treatment time and appliance type which were used in the treatment such that a timeline is correlated to display the appliance type used at a selected treatment time during a progression of the treatment with detail information about the appliance including a manufacturer of the appliance type; displaying in the case card to the user, wherein the case card provides a contact to the manufacturer which is contacted by the user directly through the network via the case card; presenting at least two of the case cards selected from the one or more case cards for comparison by the user; receiving one or more comments or observations from the user relating to the two or more case cards being compared; and associating the one or more comments or observations with the two or more case cards to form a theory card.

21. The method of claim 20 wherein the one or more parameters further include treatment-related information.

22. The method of claim 21 wherein the treatment-related information includes at least treatment time and product type.

23. The method of claim 20 further comprising forming an animation which illustrates a change from the initial condition to the final condition based upon the one or more parameters prior to displaying the one or more case cards.

24. The method of claim 20 wherein receiving from a user comprises receiving the one or more parameters to a computer system via a network.

25. The method of claim 20 further comprising soliciting a third-party for additional comments or observations relating to the two or more case cards being compared.

26. The method of claim 25 further comprising associating the additional comments or observations with the theory card.

27. The method of claim 20 further comprising associating one or more products related to the treatment of interest to form the product card.

28. A computer-implemented method of forming a case card, comprising: receiving from a user via a network one or more parameters relating to a treatment and to treatment-related information previously performed upon a subject, the one or more parameters including at least an initial condition of the subject prior to a treatment and at least a final condition of the subject upon completion of the treatment; associating one or more keyword searchable parameters with the treatment previously performed such that the case card is electronically retrievable via the network by another user not associated with the treatment previously performed; forming an animation which illustrates a change from the initial condition to the final condition based upon the one or more parameters; associating the animation with the one or more parameters within the case card; displaying the animation within the case card; and displaying a timeline of the treatment applied over a course of the treatment such that the animation is displayed within a first region of the case card and the timeline is displayed within a second region of the case card in proximity to the first region, wherein the timeline is correlated to a progression of the treatment from the initial position to the final position such that the timeline is manipulatable by the user to display one or more intermediate positions of the oral or maxillofacial region, and wherein the treatment-related information includes at least treatment time and appliance type which were used in the treatment such that the timeline is further correlated to display the appliance type used at a selected treatment time during the progression of the treatment with detail information about the appliance including a manufacturer of the appliance type, and displaying in the case card to the user, wherein the case card provides a contact to the manufacturer which is contacted by the user directly through the network via the case card.

* * * * *